(12) United States Patent
Boyle et al.

(10) Patent No.: US 6,645,223 B2
(45) Date of Patent: Nov. 11, 2003

(54) DEPLOYMENT AND RECOVERY CONTROL SYSTEMS FOR EMBOLIC PROTECTION DEVICES

(75) Inventors: William J. Boyle, Fallbrook, CA (US); Benjamin C. Huter, Murrieta, CA (US); Charles R. Peterson, Murrieta, CA (US); Donald E. Schwarten, Saratoga, CA (US); Richard S. Stack, Chapel Hill, NC (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 63 days.

(21) Appl. No.: 09/845,758

(22) Filed: Apr. 30, 2001

(65) Prior Publication Data

US 2002/0161389 A1 Oct. 31, 2002

(51) Int. Cl.$^7$ .............................................. A61M 29/00
(52) U.S. Cl. ....................................................... 606/200
(58) Field of Search ................................ 606/200, 159, 606/108, 198, 192, 194, 195; 604/96.01, 500, 22, 104

(56) References Cited

U.S. PATENT DOCUMENTS

| | | | | |
|---|---|---|---|---|
| 5,304,140 A | * | 4/1994 | Kugo et al. | 604/529 |
| 5,330,482 A | * | 7/1994 | Gibbs et al. | 606/113 |
| 5,433,723 A | * | 7/1995 | Lindenberg et al. | 606/198 |
| 5,833,694 A | * | 11/1998 | Poncet | 623/1.11 |
| 6,120,522 A | * | 9/2000 | Vrba et al. | 606/190 |
| 6,221,006 B1 | * | 4/2001 | Dubrul et al. | 600/159 |
| 6,245,100 B1 | * | 6/2001 | Davila et al. | 623/1.13 |
| 6,264,671 B1 | * | 7/2001 | Stack et al. | 606/198 |
| 6,277,138 B1 | * | 8/2001 | Levinson et al. | 606/200 |
| 6,277,139 B1 | * | 8/2001 | Levinson et al. | 606/200 |
| 6,306,106 B1 | * | 10/2001 | Boyle | 600/585 |
| 6,383,206 B1 | * | 5/2002 | Gillick et al. | 606/200 |
| 6,394,978 B1 | * | 5/2002 | Boyle et al. | 604/103.06 |
| 6,428,552 B1 | * | 8/2002 | Sparks | 606/159 |
| 6,428,559 B1 | * | 8/2002 | Johnson | 606/200 |
| 6,454,775 B1 | * | 9/2002 | Demarais et al. | 606/128 |
| 6,458,137 B1 | * | 10/2002 | Klint | 606/108 |
| 6,485,501 B1 | * | 11/2002 | Green | 606/200 |
| 6,494,885 B1 | * | 12/2002 | Dhindsa | 606/127 |
| 6,506,203 B1 | * | 1/2003 | Boyle et al. | 606/200 |
| 6,511,496 B1 | * | 1/2003 | Huter et al. | 606/200 |

* cited by examiner

*Primary Examiner*—John J. Calvert
*Assistant Examiner*—Alissa L. Hoey
(74) *Attorney, Agent, or Firm*—Fulwider Patton Lee & Utecht, LLP (57) ABSTRACT

A deployment control system provides controlled deployment of an embolic protection device which may include a guide wire, an expandable filter attached to the guide wire near its distal end, and a restraining sheath that maintains the expanded filter in a collapsed position. The deployment control system includes a torque control device which allows the physician to torque the guide wire into the patient's anatomy and a mechanism for preventing the guide wire from buckling as the restraining sheath is being retracted to deploy the expandable filter. A recovery control system for recovering the embolic protection device includes an inner catheter which extends within a lumen of an outer recovery sheath in a coaxial arrangement. A distal portion of the inner catheter extends beyond another recovery sheath during advancement of the recovery system into the vasculature. The recovery sheath can be advanced over the inner catheter to collapse the expandable filter. The proximal ends of the inner catheter and recovery sheath include handle portions having snap mechanisms which hold the components together as the recovery system is being advanced into the patient's vasculature.

34 Claims, 7 Drawing Sheets

DEPLOYMENT AND RECOVERY CONTROL SYSTEMS FOR EMBOLIC PROTECTION DEVICES

BACKGROUND OF THE INVENTION

The present invention relates generally to filtering devices and systems which can be used when an interventional procedure is being performed in a stenosed or occluded region of a body vessel to capture embolic material that may be created and released into the vessel during the procedure. The present invention is more particularly directed to deployment and recovery control systems which can be used in conjunction with such embolic filtering devices. The present invention is particularly useful when an interventional procedure, such as balloon angioplasty, stenting procedures, laser angioplasty or atherectomy, is being performed in a critical body vessel, such as the carotid arteries, where the release of embolic debris into the bloodstream can occlude the flow of oxygenated blood to the brain, resulting in grave consequences to the patient. While the recovery and deployment systems of the present invention are particularly useful in carotid procedures, the inventions can be used in conjunction with any vascular interventional procedure in which an embolic risk is present.

Numerous procedures have been developed for treating occluded blood vessels to allow blood to flow without obstruction. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed blood vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during laser angioplasty, sometimes particles are not fully vaporized and thus enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris that is carried by the bloodstream to distal vessels of the brain can cause these cerebral vessels to occlude, resulting in a stroke, and in some cases, death. Therefore, although cerebral percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the vacuum catheter does not remove all of the embolic material from the bloodstream. Also, a powerful suction could cause trauma to the patient's vasculature. Still other techniques which have had some limited success include the placement of a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel. Additionally, the recovery apparatus should be relatively flexible to avoid straightening of the body vessel. Recovery devices which are too stiff can cause trauma to the vessel walls as the filter is being collapsed and removed from the vasculature.

Some prior art expandable filters vessel are attached to the distal end of a guide wire or guide wire-like tubing that allows the filtering device to be placed in the patient's vasculature as the guide wire is steered by the physician. Once the guide wire is in proper position in the vasculature, the embolic filter can be deployed to capture embolic debris. Some embolic filter devices which utilize a guide wire for positioning also utilize the restraining sheath to maintain the expandable filter in a collapsed position. Once the proximal end of the restraining sheath is retracted by the physician, the expandable filter will move into its fully expanded position within the patient's vasculature. The restraining sheath can then be removed from the guide wire allowing the guide wire to be used by the physician to deliver interventional devices, such as a balloon angioplasty dilatation catheter or a stent delivery catheter, into the area of treatment. After the interventional procedure is completed, a recovery sheath can be delivered over the guide wire using over-the-wire techniques to collapse the expanded filter for removal from the patient's vasculature. As mentioned above, the recovery device, i.e., the recovery sheath, should be relatively flexible to track over the guide wire and to avoid straightening the body vessel once it is in place.

When a combination of an expandable filter and guide wire is utilized, it is important that the guide wire be rotatable so that the physician can steer it downstream of the area of treatment using techniques well known in the art. In this regard, the guide wire is usually "torqued" by the physician to point or steer the distal end of the guide wire into the desired body vessel. Often, when the restraining sheath is utilized, it is difficult to properly turn the composite device to deliver the filter through the tortuous anatomy of the patient. Moreover, during delivery, it is imperative that the restraining sheath remain positioned over the collapsed filter, otherwise the filter could be deployed prematurely in an undesired area of the patient's vasculature. This occurrence can cause trauma to the walls of the patient's vasculature and would require the physician to re-sheath the expanded filter to further advance the filter into the desired area. Moreover, if the physician does not have an adequate mechanism or handle at the proximal end of the composite filter device for steering the device through the tortuous anatomy, there can be unwanted buckling of the guide wire at the proximal end. Additionally, as the restraining sheath is being retracted, the physician has to be careful not to buckle or bend the guide wire. These types of occurrences during delivery and deployment of the embolic protection device are certainly undesirable.

What has been needed are reliable deployment and recovery control systems which can be used with embolic protection devices that minimize the above-mentioned incidents from ever occurring. These systems should be relatively easy for a physician to use and should provide failsafe systems for deploying the embolic filtering device into the desired area of the vessel and retrieving the same device without releasing any captured embolic debris into the body vessel. Moreover, such systems should be relatively easy to deploy and remove from the patient's vasculature. The inventions disclosed herein satisfy these and other needs.

SUMMARY OF THE INVENTION

The present invention provides deployment and recovery control systems for use with embolic filtering devices and systems for capturing embolic debris created during the performance of a therapeutic interventional procedure, such as a balloon angioplasty or stenting procedure, in a body vessel. The systems of the present invention are particularly useful when an interventional procedure is being performed in critical arteries, such as the carotid arteries, in which vital downstream blood vessels can easily become blocked with embolic debris, including the main blood vessels leading to the brain. The present invention provides the physician with a deployment control system which can be used with an embolic protection device that generally includes a guide wire having a distal end, an expandable filter attached to the guide wire near its distal end, and a restraining sheath that maintains the expandable filter in a collapsed position until it is ready to be deployed within the patient's vasculature. The recovery control system of the present invention can be used to collapse and retrieve the expanded filter once the interventional procedure has been completed. The present invention provides the physician with control mechanisms that enhance the ease of deploying and recovering the embolic protection device while providing novel features, described below which are beneficial during delivery and recovery of the embolic protection device.

The deployment control system of the present invention provides a number of benefits to the physician which include better handling of the guide wire/embolic protection device from the proximal end where the physician manipulates the guide wire for steering purposes. In this regard, the physician is better able to torque the guide wire of the embolic protection device to steer the coil tip of the guide wire into the desired body vessel during delivery. The deployment control system of the present invention also helps to prevent any premature deployment of the expandable filter which may occur by preventing the restraining sheath from being accidentally retracted during the delivery process. Moreover, the present invention provides a mechanism for preventing the guide wire from buckling as the restraining sheath is being retracted to deploy the expandable filter. The simplicity of the deployment control system of the present invention provides advantageous benefits to the physician and provides a virtual failsafe system for safely delivering and deploying the embolic protection device with the patient's vasculature.

The recovery control system of the present invention utilizes an inner catheter which is capable of being introduced over the guide wire, along with a recovery sheath which extends co-axially over the inner catheter. The inner catheter is capable of being loaded inside a lumen of the recovery sheath. In use, a distal portion of the inner catheter extends beyond the distal end of the recovery sheath allowing the inner catheter to initially approach the expanded filter which has been deployed within the patient's vasculature. Once the inner catheter has been placed near the expandable filter, the recovery control mechanism can be locked onto the guide wire and held stable as the recovery sheath is advanced distally over the expanded filter to collapse it for removal from the patient. In this manner, the recovery sheath is advanced over the inner catheter allowing the collapse of the expandable filter to be smoother and less likely to result in any trapped embolic debris being released back into the body vessel as the recovery sheath is advanced over the filter. The proximal ends of the inner catheter and outer restraining sheath include handle portions having snap mechanisms which holds the two components together as the components are being moved into the patient's vasculature for recovery purposes. The proximal handles facilitate the ease in which the physician can collapse and retrieve the expandable filter from the patient's vasculature.

The method of using the deployment control system to deliver and deploy an embolic protection device into a patient's vasculature includes loading a deployment control system onto an embolic protection device which includes a guide wire, an expandable filter assembly located near the distal end of the guide wire, and a restraining sheath for maintaining the expandable filter in a collapsed position. The deployment control system includes a torque control device attached to the guide wire near its proximal end and a spacer member disposed between the torque control device and the proximal end of the restraining sheath. The method includes introducing the composite deployment control system/embolic protection device into the patient's vasculature and advancing the distal portion of the embolic protection device into the desired location in the body vessel, usually downstream of an area to be treated. The spacer member can then be removed from the guide wire allowing the restraining sheath to be retracted proximally towards the torque control device in order to deploy the expandable filter assembly. In one aspect of the present invention, a wire introducer can be placed between the torque control device and the proximal end of the restraining sheath to provide a stiffening structure for the guide wire to prevent buckling or bending of the guide wire as the proximal end of the restraining sheath is being retracted back towards the torque control device. The deployment control system and recovery sheath can then be removed from the guide wire to allow interventional devices to be advanced over the guide wire into the area of treatment. Thereafter, any embolic debris created during the interventional procedure should be captured in the expandable filter which has been deployed downstream from the area of treatment.

The method of using the recovery control system to collapse and retrieve an embolic protection device includes loading the inner catheter inside a recovery sheath, wherein the recovery sheath is initially placed over the inner catheter such that a distal portion of the inner catheter extends beyond the distal end of the recovery sheath. The inner catheter recovery sheath can then be introduced over the guide wire which includes an expanded filter located near its distal end. The distal end of the inner catheter is advanced to a position adjacent to the expanded filter located within the patient's vasculature. The inner catheter can then be hooked onto the guide wire. The recovery sheath can then be advanced over the distal portion of the inner catheter and over the expanded filter in order to collapse the expanded filter. The recovery sheath, inner sheath, guide wire and partially or completely collapsed filter can then be removed from the patient's vasculature.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
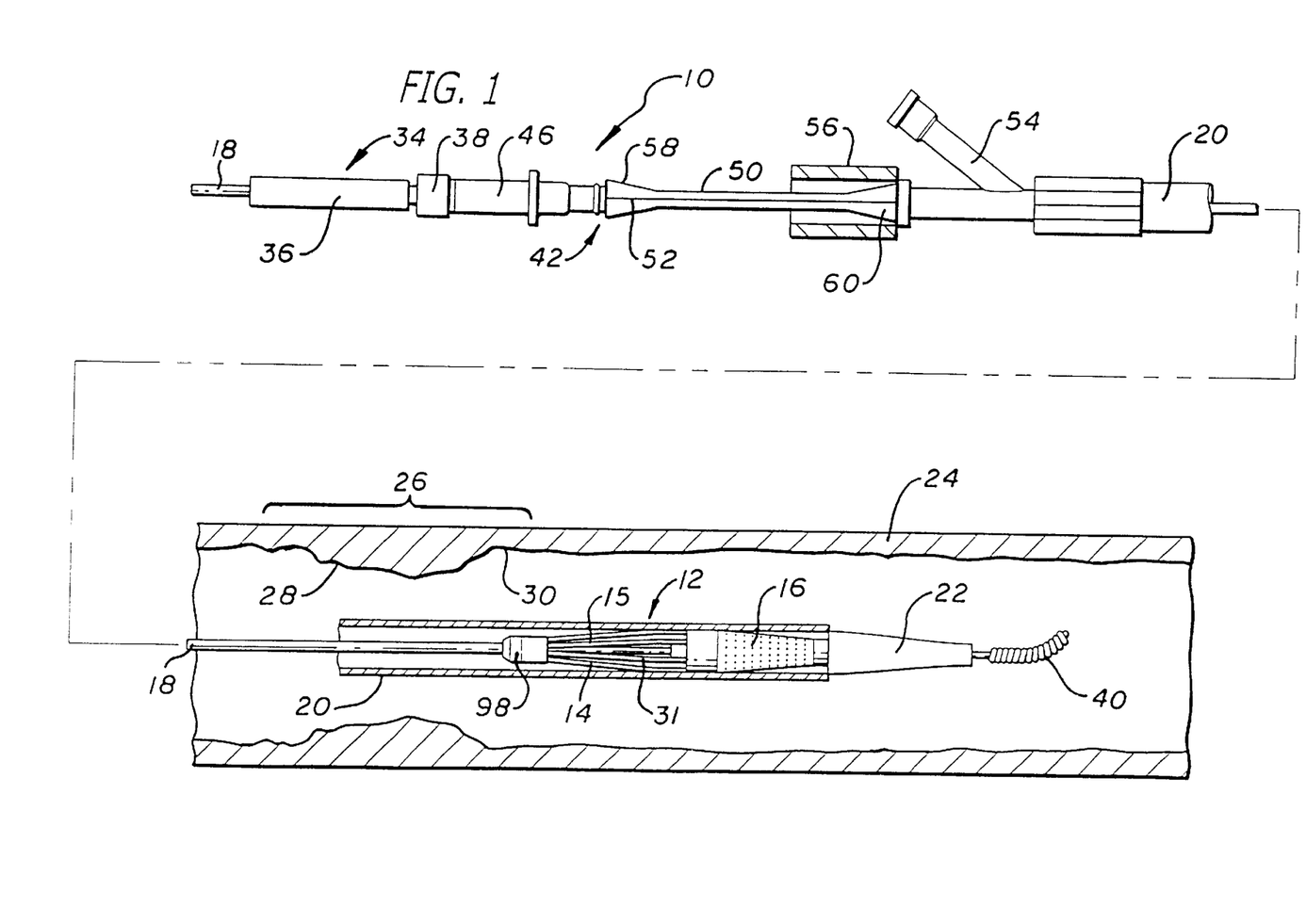
FIG. 1 is an elevational view, partially in cross section, of a deployment control system embodying features of the present invention as it is initially coupled to an embolic protection device which is being delivered for deployment past an area of treatment in a body vessel.
Figure 2:
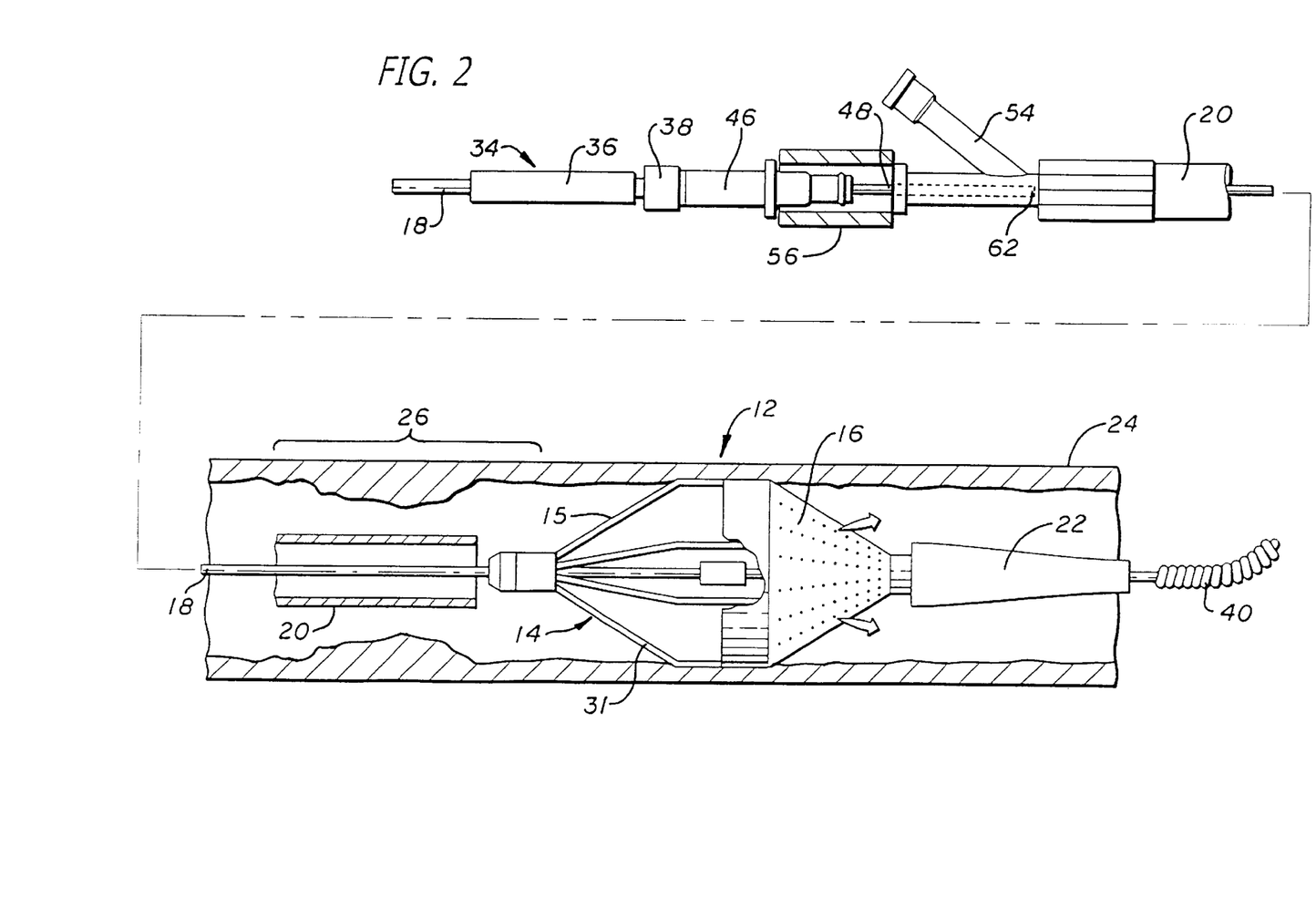
FIG. 2 is an elevational view, partially in cross section, similar to that shown in FIG. 1, wherein the deployment control system is deployed and the embolic protection device is shown in its expanded position within the body vessel.

Turning now to the drawings, in which like reference numerals represent like or corresponding elements in the drawings, FIGS. 1 and 2 illustrate a deployment control system 10 incorporating features of the present invention. This deployment control system 10 is adapted for use with an embolic protection device 12 designed to capture embolic debris which may be created and released into a body vessel during an interventional procedure. The embolic protection device 12 includes an expandable filter assembly 14 having a self-expanding strut assembly 15 and a filter element 16. In this particular embodiment, the expandable filter assembly is rotatably mounted on the distal end of an elongated tubular shaft, such as a guide wire 18. A restraining sheath 20 extends coaxially along the guide wire 18 in order to maintain the expandable filter 14 in its collapsed position until it is ready to be deployed within the patient's vasculature. The expandable filter 14 is deployed by the physician by simply retracting the restraining sheath 20 proximally to expose the expandable filter 14. The self-expanding strut assembly 15 thus becomes uncovered and immediately begins to expand within the body vessel (see FIG. 2). It should be appreciated that the embolic protection device 12 depicted herein is just one example of numerous different embolic protection devices which can be utilized in accordance with the present invention. Generally, the deployment control system and recovery control system of the present invention can be utilized in accordance with any embolic protection device which utilizes a self-expanding filter that can be deployed by, for example, retracting a sheath, sheath-like sleeve, or other mechanism which maintains the self-expanding filter in a collapsed position. An obturator 22 affixed to the distal end of the filter assembly 14 can be implemented to prevent possible "snowplowing" of the embolic protection device during delivery through the vasculature. The obturator can be made from a soft polymeric material, such as Pebax 40, and has a smooth surface to help the embolic protection device travel through the vasculature and cross lesions while preventing the distal end of the delivery catheter (not shown) from "digging" or "snowplowing" into the wall of the body vessel. Additional details regarding the particular structure and shape of the various elements making up the filter assembly 14 are provided below.

In FIG. 1, the embolic protection device 12 is shown as it is being delivered within an artery 24 or other body vessel of the patient. This portion of the artery 24 has an area of treatment 26 in which atherosclerotic plaque 28 has built up against the inside wall 30 of the artery 24. The filter assembly 14 is to be placed distal to, and downstream from, the area of treatment 26 as is shown in FIGS. 1 and 2. The therapeutic interventional procedure may comprise the implantation of a stent to increase the diameter of an occluded artery and increase the flow of blood therethrough. It should be appreciated that the embodiments of the system and method are illustrated and described herein by way of example only and not by way of limitation. Also, while the present invention is described in detail as applied to an artery of the patient, those skilled in the art will appreciate that it can also be used in body vessels, such as the coronary arteries, carotid arteries, renal arteries, saphenous veins and other peripheral arteries. Additionally, the present invention can be utilized when a physician performs any one of a number of interventional procedures, such as balloon angioplasty, laser angioplasty or atherectomy, utilizing an embolic protection device.

The strut assembly 15 may include self-expanding struts 31 which, upon release from the restraining sheath 20, expand the filter element 16 into its deployed position within the artery. When the struts 31 are expanded, the filter element 16 takes on a basket shape. Embolic debris created during the interventional procedure and released into the bloodstream are captured within the deployed filter element 16. Although not shown, a balloon angioplasty catheter can be initially introduced within the patient's vasculature in a conventional SELDINGER technique through a guiding catheter (not shown). The guide wire 18 is disposed through the area of treatment and the dilatation catheter can be advanced over the guide wire 18 within the artery 24 until the balloon portion is directly in the area of treatment 26. The balloon of the dilatation catheter can be expanded, expanding the plaque 28 against the inside wall 30 of the artery 24 to expand the artery and reduce the blockage in the vessel at the position of the plaque 28. After the dilatation catheter is removed from the patient's vasculature, a stent 32 (shown in FIG. 3) could also be delivered to the area of treatment 26 using over-the-wire techniques to help hold and maintain this portion of the artery 24 and help prevent restenosis from occurring in the area of treatment. Any embolic debris which is created during the interventional procedure will be released into the bloodstream and should enter the filter assembly 14 located downstream from the area of treatment. Once the procedure is completed, the filter assembly 14 is to be collapsed and removed from the artery 24, taking with it any embolic debris trapped within the filter element 16. The recovery control system of the present invention (described below) can be utilized to collapse the filter assembly for removal from the patient's vasculature.

The deployment control system 10 depicted in FIGS. 1 and 2 is utilized to provide controlled and accurate deployment of the filter assembly 14 of the embolic protection device 12. The system 10 includes a torque control device 34 which is manipulated by the physician in order to rotate or "torque" the guide wire 18 as the embolic protection device 12 is being delivered through the patient's vasculature. This torque control device 34 consists of a handle portion 36 and a locking mechanism 38 utilized to lock the handle portion 36 tightly on the guide wire 38. The torque control device 34 shown in FIGS. 1, 2 and 6 can be a commercially-available torque control device which is readily available. It should be appreciated by those skilled in the art that any one of a number of different torque controlled devices can be utilized in accordance with the present invention. During use, the physician manipulates the handle portion 36 allowing the physician to rotate the distal coil spring tip 40 of the guide wire 18 to steer the guide wire 18 into the proper body vessel. The physician usually creates a curvature at the distal coil spring tip 40 which is controlled by the physician via the torque control device 34. This wire introducer 42 has a structure much like a modified needle introducer. The tubular member 48 can be made from stainless steel or a polymeric material having high axial stiffness. A wire introducer 42 is located proximal to the end 44 (see FIG. 6) of the torque control device 34. The wire introducer 42 includes a proximal end cap 46 adapted to receive the distal end 44 of the torque control device 34. This wire introducer 42 includes a substantially rigid tubular member 48 (FIG. 2) which provides a stiff structure that helps prevent buckling of the guide wire as the restraining sheath 20 is retracted proximally to deploy the expandable filter assembly 14. This wire introducer 42 has a structure much like a modified needle introducer. The tubular member 48 can be made from stainless steel or a polymeric material having high axial stiffness. A spacer member 50 is located between the wire introducer 42 and the embolic protection device 12. This spacer member 50 is designed to be removed from the guide wire after the embolic protection device 12 has been steered into the proper position within the patient's vasculature. This spacer member 50, once removed from the guide wire, allows the proximal end of the embolic protection device 12 to be retracted back towards the torque control device 34 a sufficient length to uncover the expandable filter assembly 14 located at the distal end of the guide wire 18. The spacer member 50 includes a slit 52 or a perforated line that extends along the length thereof which allows the physician to remove the spacer member from the guide wire once the restraining sheath is to be retracted. This spacer member helps prevent the restraining sheath 20 from retracting proximally, thus preventing the expandable filter assembly 14 from prematuring expanding as the embolic protection device 12 is being delivered through the patient's vasculature.

Figures 9, 11:
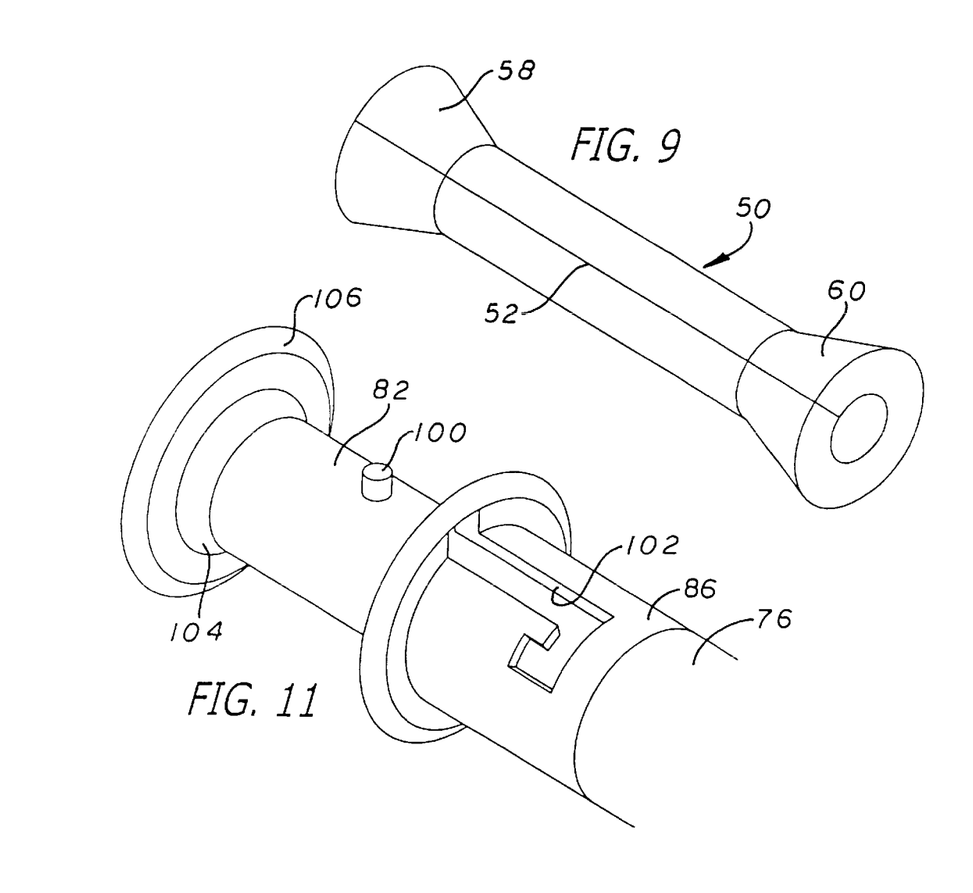
FIG. 9 is a perspective view of the spacer member shown in FIGS. 1 and 6 which is utilized in conjunction with the deployment control system of the present invention.
FIG. 11 is a perspective view of another embodiment of a locking mechanism which can be utilized in conjunction with the components of the deployment control system or recovery control system of the present invention.

As can be seen in FIGS. 1 and 2, the proximal end of the embolic protection device 12 includes a luer fitting 54 with a rotatable hemostatic valve 56 attached at its end. This rotatable hemostatic valve 56 allows the guide wire 18 to be placed within an internal lumen (not shown) of the fitting 54 while preventing backflow of blood therethrough. As can be seen in FIGS. 1 and 9, the spacer member 50 includes a flared proximal end 58 and a flared distal end 60 which come in contact with adjacent components. In FIG. 1, the flared proximal end 58 is shown contacting the end cap 46 of the wire introducer 42. In this regard, these particular elements remain in an abutting relationship until the spacer member 50 is to be removed for deployment of the filter assembly. The flared distal end 60 is in turn in contact with an opening (not shown) located on the rotatable hemostatic valve 56. The flared distal end 60 of this spacer member 50 helps prevent the spacer member 50 from entering the opening of the rotating hemostatic valve 56. When the components are in the position shown in FIG. 1, the distal end 62 of the tubular member 48 is adjacent, or in, the internal lumen (not shown) of the fitting 54. After the spacer member 50 is removed, as described below, the fitting 54 can be retracted back towards the torque control device.

Figure 10:
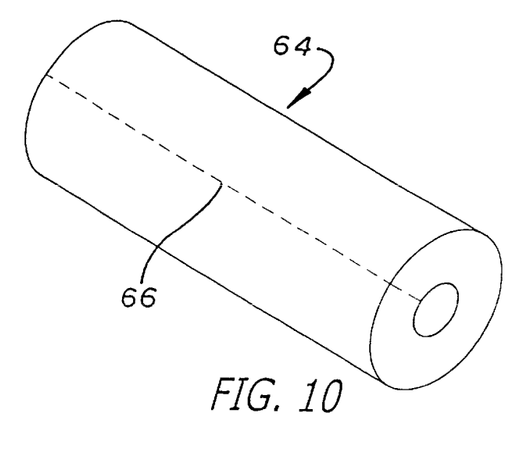
FIG. 10 is a perspective view of another embodiment of a spacer member which can be utilized in conjunction with the deployment control system of the present invention.

Referring now to FIG. 10, an alternative embodiment of the spacer member 64 is shown which lacks the flared ends utilized in the previously described embodiment. In this particular embodiment, the spacer member 64 has a substantially tubular shape and has large wall thickness which creates a large abutting shoulder that acts substantially like the flared ends in preventing the member 64 from entering the opening of the rotating hemostatic valve 56. The end of this particular spacer member 64 has a sufficient wall thickness to provide a shoulder against which the distal end 62 of the wire introducer 42 can abut. This spacer member 64 includes a perforation line 66, rather than a longitudinal slit, as is shown in the previous embodiment of the spacer marker member 50. This perforated line 66 is utilized as a similar fashion as the slit 52 in that once the spacer member 64 is to be removed from the deployment control system, the perforation line is simply torn by the physician to remove the spacer off of the guide wire. Thereafter, the proximal end of the embolic protection device 12 can be retracted to expand the filter assembly 14. It should also be appreciated to those skilled in the art that other sizes and shapes of the spacer member can be utilized without departing from the spirit and scope of the present invention. Generally, the length of the spacer member corresponds approximately to the length of restraining sheath which must be retracted in order to deploy the expandable filter assembly 14. It should be appreciated that the length of the spacer member can be increased to insure that the distal end of the restraining sheath 20 properly retracted from the expandable filter assembly 14. Additionally, the slit 52 or perforated line 66 can be cut into the spacer member in any one of a number of different sizes and shapes. For example, the slit 52 on line 66 could be a circular cut which extends around the spacer member from end to end, rather than the substantially straight line cut shown in FIGS. 9 and 10. This is just one example of the many ways that the slit or line could be cut into the spacer member without departing from the spirit and scope of the invention.

Once the spacer member has been removed from the guide wire 18, the proximal end of the embolic protection device 12 can be retracted proximally to deploy the expandable filter assembly 14. When this particular action is taken, the tubular member 48 of the wire introducer 42 acts as a stiffener to prevent the guide wire 18 from buckling or bending as the proximal end of the embolic protection device is being retracted. In this regard, there is less likelihood that the physician will buckle or place a kink in the guide wire during deployment of the embolic protection device. It should be appreciated that if the tubular member were not present, a portion of the guide wire would be exposed between the proximal fitting 54 and the end of the torque control device 34. As a result, there could be a greater possibility that the physician could buckle or otherwise bend the guide wire 18 as the proximal end of the embolic protection device is being retracted proximally towards the torque control device. In the present invention, once the proximal end of the embolic protection device is retracted back, the tubular member 48 remains in the internal lumen of the fitting 54 as the fitting and restraining sheath 20 are retracted back. Once deployment has been completed, the torque control device 34, the wire introducer 42, and restraining sheath 20 can be removed from the guide wire to allow an interventional device to be advanced into the area of treatment by the physician using over-the-wire techniques.

Figure 6:
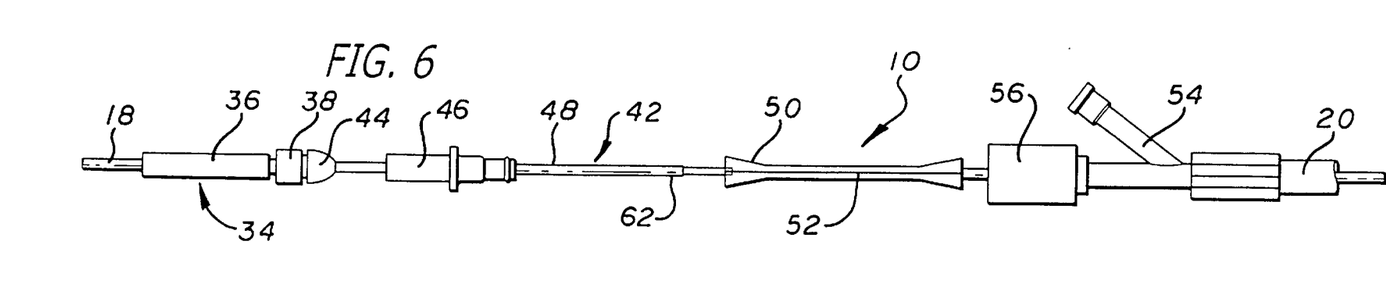
FIG. 6 is an elevational view of the various components making up the deployment control system depicted in FIGS. 1 and 2.

The torque control device 34 and wire introducer 42 are shown in FIGS. 1 and 6 as separate components which are joined together. However, it is also possible to manufacture these same two components as a single unit, if desired. Referring now to FIG. 6, the proximal end cap 46 of the wire introducer 42 can be made with a female type ball joint lock with a matching male type ball joint lock formed at the end of the torque control device 34. The male to female fittings of these two components allow for a snug fit between the same components. When the torque control device 34 is securing fastened to the guide wire, the embolic protection device 12 cannot be inadvertently deployed. This also allows the guide wire 18 to be torqued without risk of deploying the embolic protection device. Additionally, the male to female fittings of the torque control device 34 and wire introducer 42 allow the two components to rotate relative to one, another although a simple locking mechanism could also be used to prevent the torque control device 34 and wire introducer 42 to rotate simultaneously when manipulated by the physician. A locking mechanism, such as the one shown in FIG. 11 could also be implemented for locking these components together.

Figure 3:
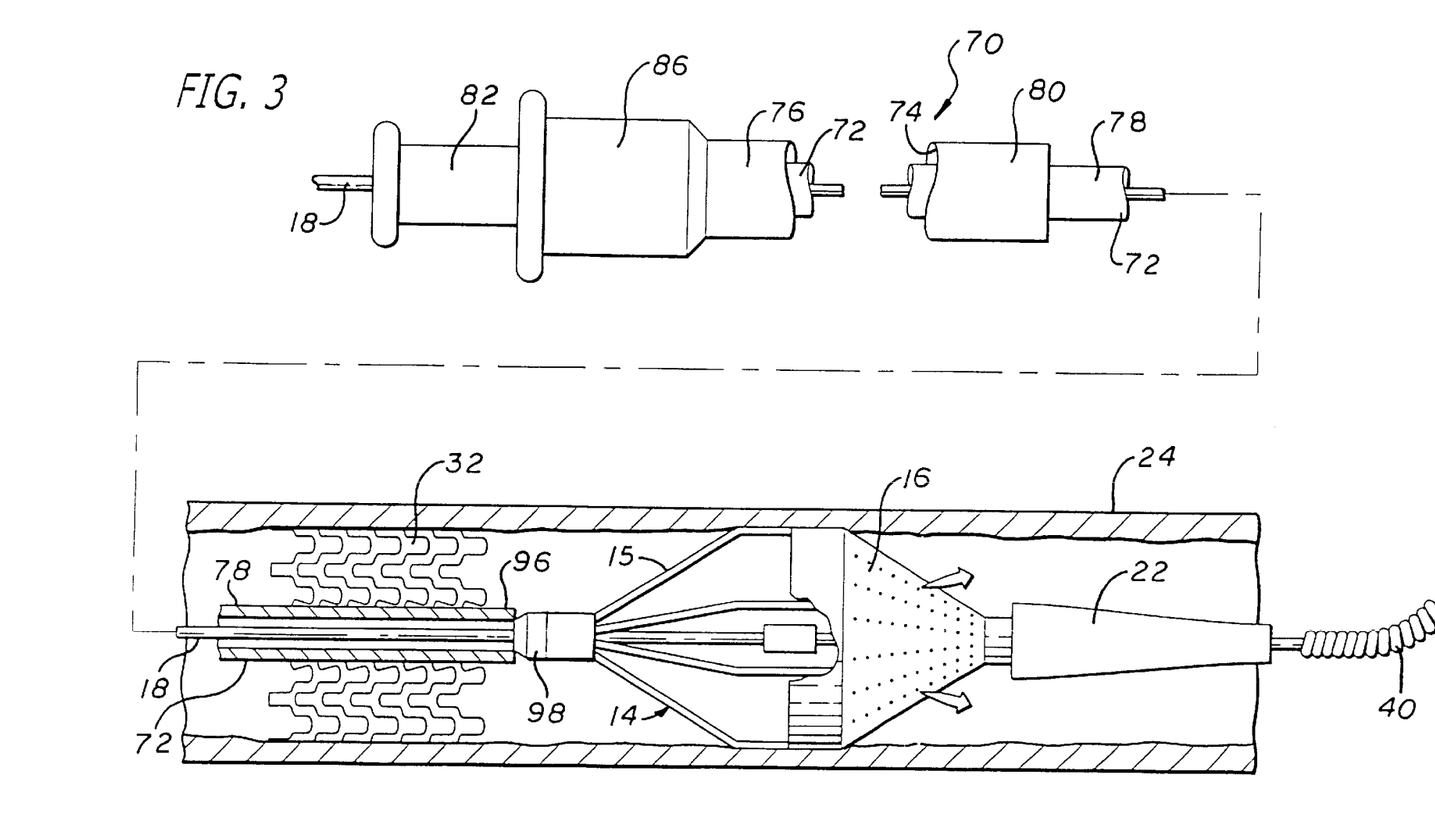
FIG. 3 is an elevational view, partially in cross section, similar to that shown in FIG. 2, wherein the deployment control system has been removed from the body vessel and a recovery control system embodying features of the present invention is being deployed to collapse and retrieve the expanded embolic protection device.
Figure 4:
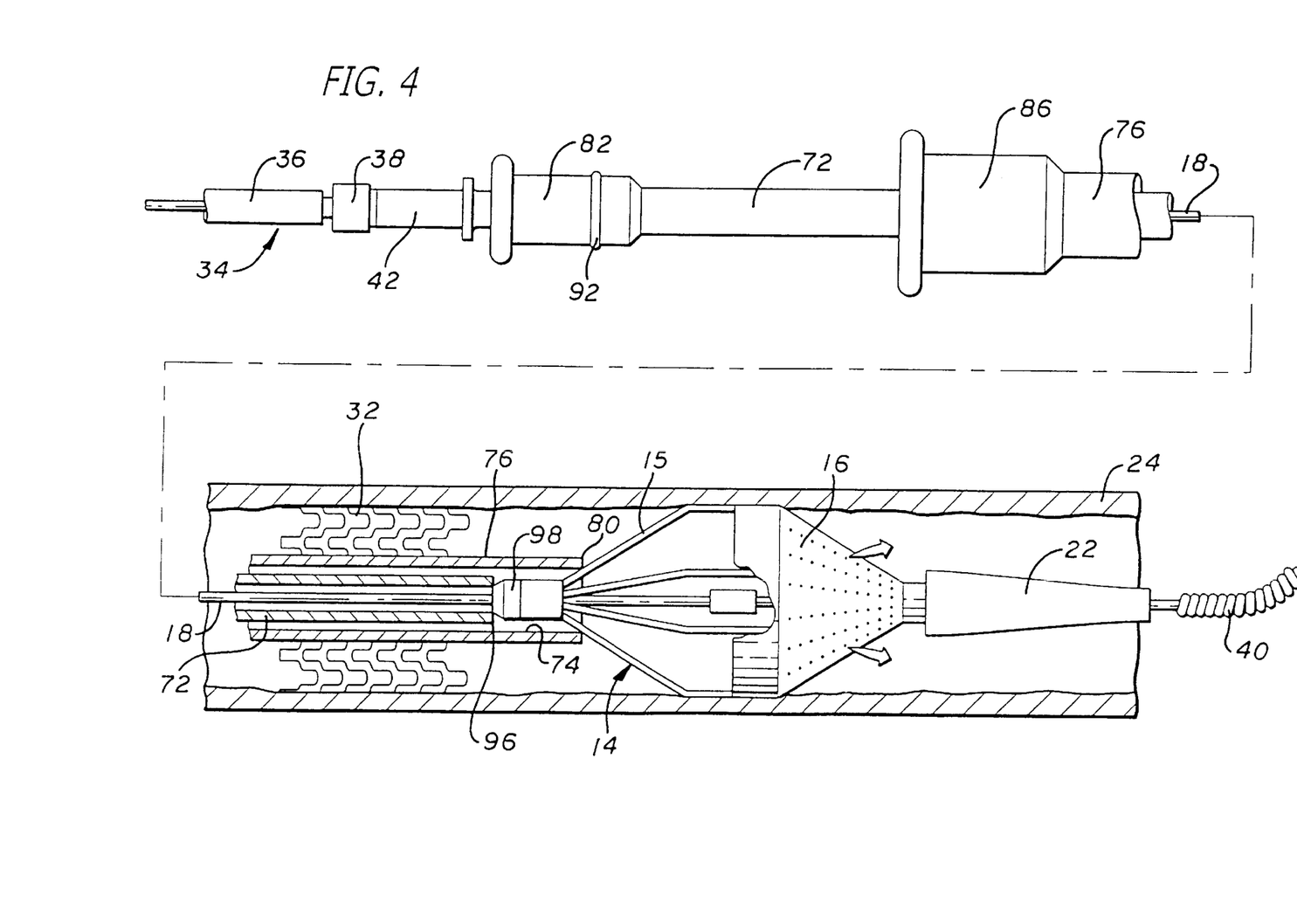
FIG. 4 is an elevational view, partially in cross section, similar to that shown in FIG. 3, wherein the recovery sheath of the recovery control system is being deployed to collapse the expanded embolic protection device.
Figure 5:
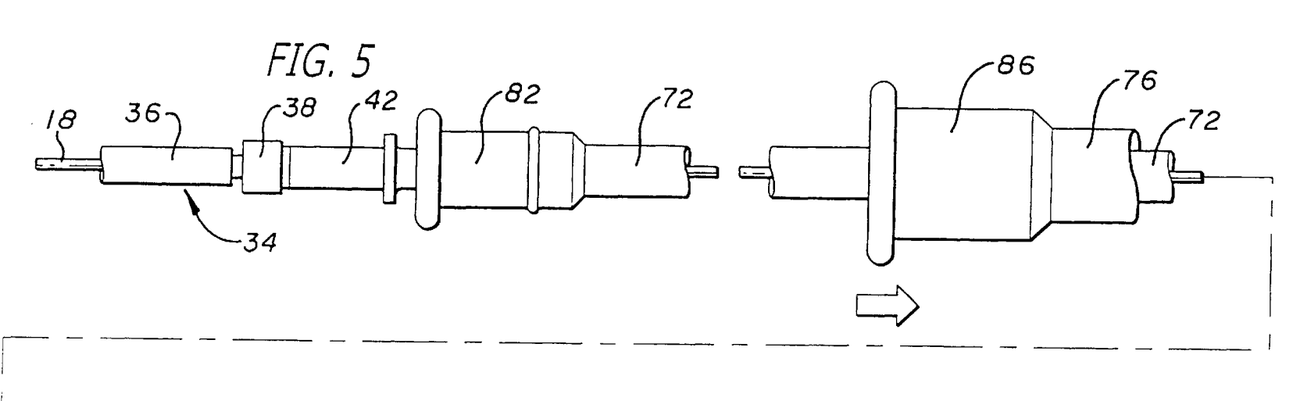
FIG. 5 is an elevational view, partially in cross section, similar to that shown in FIG. 4, wherein the recovery control system has retracted the expanded embolic protection device for removal from the body vessel.

When the embolic protection device 12 is to be removed from the vasculature, the recovery control system 70 of the present invention can be utilized. Referring now to FIGS. 3 to 5, the recovery system 70 includes an inner catheter 72 which is loaded inside a lumen 74 of a recovery sheath 76. The recovery sheath 76 is advanced over the inner catheter 72 and filter assembly 14 to collapse and recover the filter assembly 14. The recovery sheath 76 has a larger inner diameter than the outer diameter of inner catheter 72. The recovery sheath 76 can have a working length which may be up to 10 to 15 centimeters shorter than the inner catheter 72. This allows a distal portion 78 of the inner catheter 72 to extend beyond the distal end 80 of the recovery sheath 76 during initial delivery through the artery, as will be described below.

Figure 7:
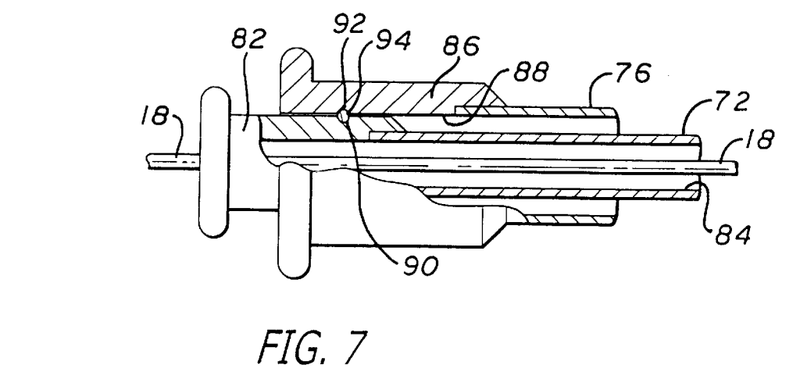
FIG. 7 is an elevational view, partially in cross-section and fragmented, of the proximal handle components of the recovery control system shown in FIG. 3.
Figure 8:
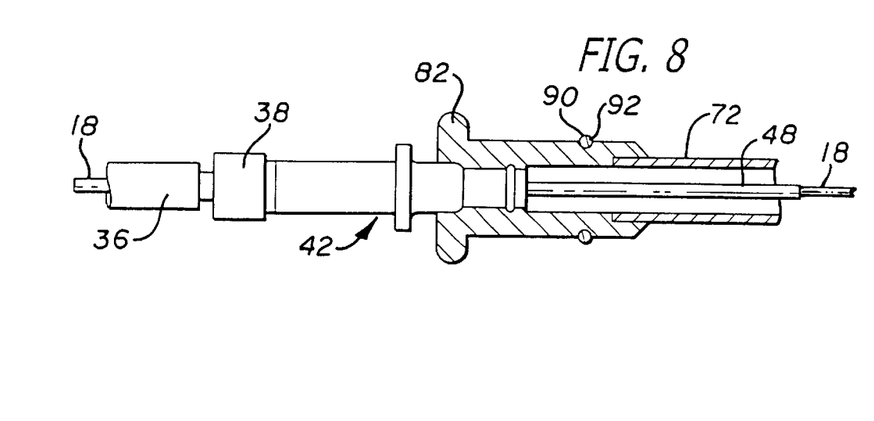
FIG. 8 is an elevational view, partially in cross-section and fragmented, showing the components of the recovery control system shown in FIG. 4.

The proximal ends of the recovery control system 70 include handles which allow the physician to easily manipulate the components when retrieving the embolic protection device 12. The inner catheter 72 includes a control handle 82 which includes a lumen 84 (see FIG. 7) which is backloaded onto the guide wire 18. The recovery sheath 76 has a similar proximal control handle 86 which extends over the proximal handle 82 of the inner catheter 72 in a coaxial arrangement. Likewise, the control handle 86 of the recovery sheath 76 includes an internal lumen 88 (see FIGS. 7 and 8) which receives the inner catheter 72. In use, the physician is able to hold these proximal handles 82 and 86 when the embolic protection device 12 is to be collapsed and retrieved for removal from the patient's vasculature. In this regard, a locking mechanism, such as the one shown in FIGS. 7 and 8 can be utilized. The simple mechanism which is utilized includes a male female lock joint which is located on the proximal handles 82 and 86. In this regard, the proximal control handle 82 includes a recess 90 for receiving such as an O-ring 92 which sits within the recess 92. Likewise, the proximal control handle 86 includes a recess 94 which is adapted to receive the portion of the O-ring 92 which extends above the surface of the proximal handle 82. In this regard, the O-ring 92 acts as a simple locking mechanism for maintaining the two components, namely the proximal control handles 82 and 86, together until the physician is ready to advance the restraining sheaths 76 distally towards the filter assembly 14. It should be appreciated that other locking mechanisms, for example, the one shown in FIGS. 1 and 11, can be utilized without departing from the spirit and scope of the present invention.

The inner catheter 72 is first introduced over the guide wire 18 for delivery past the treatment site 26, where, for example, a stent 32 has been implanted. As shown in FIG. 3, the relatively flexible distal portion 78 of the inner catheter 72 tracks over the guide wire 18 distally from the recovery sheath 76. The inner catheter 72 can be less stiff than the recovery sheath 76 and the distal portion 78 of the inner catheter 72 is likely to cause less straightening of the vasculature as it tracks over the guide wire 18 to the expandable filter assembly 14. The delivery of this smaller diameter inner catheter 72 helps to maintain the curvature of the artery by minimizing the possibility of the artery "straightening" as the larger diameter recovery sheath 76 is advanced over the distal portion 78. While the "straightening" effect of the artery is not apparent from the drawings (since the artery 24 is shown relatively straight to begin with), it should be appreciated that this straightening effect would be less likely to occur when the filter assembly is in a curved artery due to the presence of the inner catheter 72. Additionally, the increased flexibility of the inner catheter 72 better enables the distal portion of the inner catheter 72 to negotiate the tortuous anatomy of the vasculature and improves tracking over the guide wire 18.

As shown in FIGS. 4 and 5, after the distal end 96 of the inner catheter 72 has reached the proximal fitting 98 which maintains the filter assembly 14 on the guide wire 18, the inner catheter 72 can be then locked into place by the physician. This is accomplished by backloading the torque control device 34 with the wire introducer 42 onto the guide wire 18 and positioning the two components in an abutting relationship with the proximal control handle 82 of the inner catheter 72. Once the torque control device 34 and wire introducer 42 are placed adjacent to the proximal handle 82, the physician can lock the torque control device 34 via the locking mechanism 38 to lock the components onto the wire 18. In this regard, the inner catheter 72 cannot move along the length of the guide wire since the distal end 46 is in an abutting relationship with the proximal fitting 98 and the proximal control handle 82 is in an abutting relationship with the torque control device 34 and wire introducer 32. Once the inner catheter 72 is locked in place, the recovery sheath 76 can now be advanced over the distal portion 78 of the inner catheter 72 and toward the filter assembly 14 in order to collapse and recover the expanded filter assembly 14. The column strength at the distal end 80 of the recovery sheath 76 should be sufficiently strong to ensure that as the struts of the filter assembly 14 are moved back into its collapsed position and that the recovery sheath 76 does not buckle or experience an accordion effect.

The collapse of the expandable filter assembly 14 can be accomplished by the physician by holding the proximal control handle 82 and moving the proximal end control handle 86 of the recovery sheath 76 forward to move the distal end 80 of the sheath 76 over the filter assembly 14, as shown in FIG. 5. Upon collapse of the filter assembly 14, any embolic debris generated during the interventional procedure will remain trapped inside the filter element 16. The recovery system 70, along with the embolic protection device 12, can then be withdrawn from the bloodstream and removed from the vasculature.

Referring now to FIG. 11, an alternative embodiment of a locking mechanism which can be utilized in conjunction with the components of deployment control system or recovery control system is shown. In this particular figure, the proximal control handle 82 includes a raised locking pin 100 which is adapted to move through a slot 102 which is formed on the proximal control handle 86 of the recovery sheath 76. As can be seen in FIG. 11, the slot 102 is J-shaped in order to lock the locking pin, this locking the two control handles 82 and 86 together during use. A resilient member 104 placed near the distal end 106 of the control handle 82 creates a biasing force on the two components to maintain the locking pin 100 within the slot 102 during usage. This resilient member 104 can be in the shape of an O-ring, or any other appropriate shape. It should be appreciated that the resilient member 104 provides a biasing force on the ends of each of the control handles 82 and 86 to lock the two components in place. Thereafter, if the physician wishes to decouple the two control handles, he/she needs to compress the member 104 a short distance to allow the locking pin 100 to be removed from the end of the J-shaped slot 102 where it can then be removed from the slot 102 altogether. Thereafter, the control handle 86 of the recovery sheath 76 can be moved distally, as needed, to recover the expanded filter assembly 14 of the embolic protection device 12. It should be appreciated by those skilled in the art that similar type locking mechanisms can be used in conjunction with the other components of the deployment control system 10. For example, a similar locking mechanism can be implemented on the torque control device 34 and the wire introducer 42 in order to lock the two components as needed. Still other types of locking mechanisms could be utilized in accordance with the present invention in order to achieve the same desired locking feature.

It should be appreciated that there is a desire to reduce the overall profile of the composite inner catheter/recovery sheath so it would be beneficial to use as small a wall thickness as possible to reduce the profile of the recovery system. However, it should be appreciated that the strength of the recovery sheath still must be sufficient to maintain the filtering assembly of the embolic protection device in a collapsed state for removal from the patient's vasculature.

The materials which can be utilized for the restraining and recovery sheaths and inner catheter include polymeric material which are well known in the art. One suitable polymeric material is cross-linked HDPE. Alternatively, the recovery and restraining sheath and inner catheter can be made from materials such as polyolefin which has sufficient strength to hold the compressed strut assembly and has relatively low frictional characteristics to minimize any friction between the filtering assembly and the sheath. Polyamide could be used for the inner catheter as well. Friction can be further reduced by applying a coat of silicone lubricant, such as Microglide®, to the inside surface of the recovery sheath before the recovery sheath is placed over the filter assembly. Still other suitable materials could be utilized for either the recovery sheath and inner catheter without departing from the spirit and scope of the present invention. Preferably, the wall thickness of the inner catheter is smaller than the recovery sheath to increase the flexibility as the composite recovery sheath/inner catheter is being delivered through the tortuous anatomy. However, depending upon the type of material which is utilized, the wall thickness of the inner catheter could be same or even greater than that of the recovery sheath. As is shown in the drawings, the inner catheter can be made from an elongated tubing which is sufficiently flexible to travel over the guide wire. Other embodiments of the inner catheter can be utilized without departing from the spirit and scope of the present invention.

The other components of the deployment control system and recovery system can be made from suitable plastic materials which are readily available in the art. For example, the proximal handles of the inner catheter and recovery sheath can be made from plastic materials which are commonly used for medical products. The components of the deployment control system can also be made from materials which are currently being used to manufacture similar medical devices.

In view of the foregoing, it is apparent that the systems of the present invention substantially enhance the safety and efficiency of deploying and recovering embolic protection devices which are used to collect embolic material that may be generated during an interventional procedure. Further modifications and improvements may additionally be made to the system and method disclosed herein without departing from the scope of the present invention. Accordingly, it is not intended that the invention be limited, except as by the appended claims.

What is claimed is:

1. A system for deploying within a body vessel an embolic protection device, which includes a guide wire, an expandable filter disposed on the guide wire, and a retractable restraining sheath for maintaining the expandable filter in a collapsed position, comprising:
a torque control device adapted to be connected to the guide wire for rotating the guide wire; and
a spacer member placed between the torque control device and the restraining sheath for preventing the restraining sheath from moving proximally on the guide wire until the spacer member is removed.

2. The system of claim 1, further including:
a wire introducer associated with the torque control device, the wire introducer having a tubular member which extends distally away from the torque control device to help prevent the guide wire from bending when the restraining sheath is retracted proximally on the guide wire towards the torque control handle.

3. The system of claim 1, further including:
means associated with the torque control device to help prevent the guide wire from bending when the restraining sheath is retracted proximally on the guide wire towards the torque control handle.

4. The system of claim 2, further including:
means for locking the torque control device to the wire introducer.

5. The system of claim 1, wherein:
the spacer member has a longitudinal length equal to or greater than the longitudinal length of the filter assembly.

6. The system of claim 1, wherein:
the restraining sheath has a proximal end and the spacer member has a first end and a second end, the second end being in abutting relationship with the proximal end of the restraining sheath.

7. The system of claim 2, wherein:
the restraining sheath has a proximal end and the spacer member has a first end and a second end, the second end being in abutting relationship with the proximal end of the restraining sheath and the first end being in abutting relationship with the end of the tubular member of the wire introducer.

8. The system of claim 4, wherein:
a fitting forms the proximal end of the restraining sheath.

9. The system of claim 8, wherein:
a fitting forms the proximal end of the restraining sheath.

10. The system of claim 1, wherein:
the spacer member has a lumen through which the guide wire extends and a slit extending therethrough for allowing the spacer member to be removed from the guide wire.

11. The system of claim 1, wherein:
the spacer member has a lumen through which the guide wire extends and a perforated score line extending therethrough which is capable of tearing to allow the spacer member to be removed from the guide wire.

12. The system of claim 1, further including:
means for locking the torque control device onto the guide wire.

13. The system of claim 1, wherein:
the spacer member has a first end and a second end, each first and second ends having an outwardly extending flare for creating an extended shoulder region.

14. An embolic protection system, comprising:
a guide wire having a distal end;
an expandable filter located near the distal end of the guide wire;
a restraining sheath extending over the guide wire in a coaxial arrangement and adapted to maintain the expandable filter in a collapsed position, the restraining sheath having a proximal end and a distal end;
a torque control device adapted to be connected to the guide wire for rotating the guide wire; and
a spacer member adapted to be removably connected to the guide wire and placed between the torque control device and the proximal end of the restraining sheath for preventing the restraining sheath from moving proximally on the guide wire until the spacer member is removed from the guide wire.

15. The system of claim 14, further including:
a wire introducer associated with the torque control device, the wire introducer having a tubular member which extends distally away from the torque control device to help prevent the guide wire from bending when the restraining sheath is retracted proximally towards the torque control handle.

16. The system of claim 15, wherein:
the restraining sheath has a proximal end and the spacer member has a first end and a second end, the second end being in abutting relationship with the proximal end of the restraining sheath and the first end being in abutting relationship with the end of the tubular member of the wire introducer.

17. The system of claim 16, wherein:

a fitting forms the proximal end of the restraining sheath.

18. The system of claim 14, further including:

means associated with the torque control device to help prevent the guide wire from bending when the restraining sheath is retracted proximally on the guide wire towards the torque control handle.

19. The system of claim 14, further including:

means for locking the torque control device to the wire introducer.

20. The system of claim 14 wherein:

the spacer member has a longitudinal length equal to or greater than the longitudinal length of the filter assembly.

21. The system of claim 14, wherein:

the restraining sheath has a proximal end and the spacer member has a first end and a second end, the second end being in abutting relationship with the proximal end of the restraining sheath.

22. The system of claim 21, wherein:

a fitting forms the proximal end of the restraining sheath.

23. The system of claim 14, wherein:

the spacer member has a lumen through which the guide wire extends and a slit extending therethrough for allowing the spacer member to be removed from the guide wire.

24. The system of claim 14, wherein:

the spacer member has a lumen through which the guide wire extends and a perforated score line extending therethrough which is capable of tearing to allow the spacer member to be removed from the guide wire.

25. The system of claim 14, further including:

means for locking the torque control device onto the guide wire.

26. The system of claim 14, wherein:

the spacer member has a first end and a second end, each first and second ends having an outwardly extending flare for creating an extended shoulder region.

27. A method for deploying within a body lumen an embolic protection device, which includes a guide wire, an expandable filter disposed on the guide wire, and a restraining sheath for maintaining the expandable filter in a collapsed position, comprising:

placing a deployment control system on the guide wire proximal to the expandable filter, the deployment control system including a torque control device for rotating the guide wire and a spacer member disposed between the torque control device and the proximal end of the restraining sheath;

introducing the embolic protection device with the attached deployment control system into the body vessel;

advancing the expandable filter of the embolic protection device to the desired location in the body vessel;

removing the spacer member from the guide wire; and moving the restraining sheath proximally toward the torque control device to retract the retaining sheath and deploy the expandable filter within the body vessel.

28. The method of claim 27, wherein:

the deployment control system further includes a wire introducer disposed between the torque control device and spacer member, the wire introducer having a tubular member which extends distally away from the torque control device to help prevent the guide wire from bending when the restraining sheath is moved proximally on the guide wire towards the torque control handle.

29. The method of claim 28, wherein:

the restraining sheath has a proximal fitting for receiving the guide wire and the spacer member has a first end and a second end, the second end being in abutting relationship with the fitting of the restraining sheath and the first end being in abutting relationship with the end of the tubular member of the wire introducer when the embolic protection device is introduced into the body vessel.

30. The method of claim 29, wherein:

the deployment control system further includes means for locking the torque control device to the wire introducer.

31. The method of claim 27 wherein:

the deployment control system further includes means for locking the torque control device to the wire introducer.

32. The method of claim 27, wherein:

the spacer member has a lumen through which the guide wire extends and a slit extending therethrough for allowing the spacer member to be removed from the guide wire.

33. The method of claim 27, wherein:

the spacer member has a lumen through which the guide wire extends and a perforated score line extending therethrough which is capable of tearing to allow the spacer member to be removed from the guide wire.

34. The method of claim 27 wherein:

after the expandable filter is deployed, the following:

removing the restraining sheath and deployment control system from the guide wire; and advancing an interventional device along the guide wire to an area to be treated within the body vessel.

* * * * *

UNITED STATES PATENT AND TRADEMARK OFFICE
CERTIFICATE OF CORRECTION

PATENT NO. : 6,645,223 B2 Page 1 of 1
DATED : November 11, 2003
INVENTOR(S) : William J. Boyle et al.

It is certified that error appears in the above-identified patent and that said Letters Patent is hereby corrected as shown below:

<u>Column 14,</u>
Line 14, delete "claim 4", and insert -- claim 7 --.
Line 16, delete "claim 8", and insert -- claim 6 --.

Signed and Sealed this

Twenty-seventh Day of April, 2004

JON W. DUDAS
*Acting Director of the United States Patent and Trademark Office*